United States Patent [19]

Hirschberg

[11] Patent Number: 5,476,499
[45] Date of Patent: Dec. 19, 1995

[54] MEDICAL ELECTRODE LEAD WITH ATRIAL ELECTRODE AT THE DISTAL AND VENTRICULAR ELECTRODE BETWEEN THE DISTAL AND PROXIMAL ENDS

[75] Inventor: Jakub Hirschberg, Taby, Sweden

[73] Assignee: Pacesetter AB, Solna, Sweden

[21] Appl. No.: 342,047

[22] Filed: Nov. 17, 1994

[30] Foreign Application Priority Data

Dec. 3, 1993 [SE] Sweden .................................. 9304031

[51] Int. Cl.$^6$ ................................. A61N 1/00; A61B 5/04
[52] U.S. Cl. ............................ 607/123; 607/14; 128/642; 128/695 R; 128/696; 128/702
[58] Field of Search ..................... 128/642, 702, 128/705, 695, 696, 700; 607/14, 32, 126, 129, 17, 123

[56] References Cited

U.S. PATENT DOCUMENTS

| | | | |
|---|---|---|---|
| 3,995,623 | 12/1976 | Blake et al. | ............................. 607/123 |
| 4,154,247 | 5/1979 | O'Neill . | |
| 4,355,646 | 10/1982 | Kallok et al. . | |
| 4,402,329 | 10/1983 | Williams | ................................. 607/123 |
| 4,444,195 | 4/1984 | Gold . | |
| 4,567,901 | 2/1986 | Harris . | |
| 4,711,027 | 12/1987 | Harris . | |
| 5,161,527 | 11/1992 | Nappholz et al. | ......................... 607/14 |

FOREIGN PATENT DOCUMENTS

| | | |
|---|---|---|
| 3049652 | 6/1987 | Germany . |
| 2187100 | 9/1987 | United Kingdom . |

Primary Examiner—Angela D. Sykes
Assistant Examiner—Stephen Huang
Attorney, Agent, or Firm—Hill, Steadman & Simpson

[57] ABSTRACT

In an electrode system for implantation in a heart, both the atrium and ventricle electrically interact with a medical apparatus. The electrode system has a single electrode lead having an atrial electrode at a distal end for implantation in the atrium before the electrode lead is advanced deeper into the heart so that a ventricular electrode in-line with and preceding the atrial electrode along the lead, is connectable in the ventricle of the heart. The electrode lead has a first curvature near the ventricular electrode and a second curvature near the atrial electrode in order to facilitate implantation of the electrode system and reduce mechanical loads on the heart after implantation. The electrode system can also be equipped with defibrillation electrodes and/or physiological sensors, thereby becoming multi-functional.

34 Claims, 3 Drawing Sheets

MEDICAL ELECTRODE LEAD WITH ATRIAL ELECTRODE AT THE DISTAL AND VENTRICULAR ELECTRODE BETWEEN THE DISTAL AND PROXIMAL ENDS

BACKGROUND OF THE INVENTION

1. Field of the Invention

The present invention relates to an electrode system, to be implanted in a heart and connected with a proximal end to a medical apparatus for monitoring, diagnosing and/or treating a heart, of the type having an electrode lead, an atrial electrode arranged on the electrode lead for electrical connection to tissue in an atrium of the heart, and a first electrode conductor arranged in the electrode lead for connecting the atrial electrode to a first contact at the proximal end.

The present invention also relates to an electrode system of the above type which further has a ventricular electrode, arranged on the electrode lead, for electrical connection to tissue in a ventricle of the heart and a second electrode conductor, arranged in the electrode lead, for connecting the ventricular electrode to a second contact at the proximal end.

2. Description of the Prior Art

The implantation of electrode systems for medical purposes in children poses a problem for conventional electrode systems. The electrode lead between the medical apparatus and heart must stretch as the child grows and thus damages tissue in the patient's body. To prevent this damage, a surplus length of electrode lead is sometimes implanted in a loop around the medical apparatus to serve as additional lead length during the child's growth. Utilizing this additional lead length, however, requires surgery to unwind the surplus length and to introduce the necessary additional length of electrode lead into a vein towards the heart.

Another problem with conventional electrode systems is the need for a plurality of electrode leads for different uses, e.g., when both the ventricle and the atrium are to be stimulated or sensed (as in DDD-systems), when the atrium is to be stimulated and a physiological parameter is to be sensed.

A large number of physiological parameters related to the heart's function is known. In addition to the electrical signals from the heart, blood pressure, blood flow, oxygen saturation, pH, blood temperature etc., are parameters of interest. A number of these parameters can advantageously be measured in the ventricle, so two electrode leads are required when the atrium is to be stimulated and a physiological parameter is to be sensed in the ventricle.

Yet another problem occurs with conventional electrode systems utilizing defibrillation electrodes to be placed in the heart for defibrillating the atrium, the ventricle or both. In particular the atrial defibrillation electrode is difficult to arrange in a steady position within the atrium.

For heart stimulators in which both the atrium and ventricle are to be stimulated and/or electrically sensed, a number of electrode systems has been devised to facilitate implantation and, primarily, to reduce the number of electrode leads which have to be implanted in the heart.

One such electrode system is described in U.S. Pat. No. 4,567,901. This electrode system has a common electrode lead which divides inside the heart into an atrial electrode lead and a ventricular electrode lead. Even if this electrode system can be manipulated into the heart during implantation, the atrial electrode and the ventricular electrode must still be positioned and affixed as if they were arranged on separate electrode leads.

Another known electrode system is described in U.S. Pat. No. 4,444,195. This electrode system has a single electrode lead with one or a plurality of ventricular electrodes at the distal end of the electrode lead and one or a plurality of atrial electrodes arranged at an appropriate distance from the distal end. The electrode lead has a slight curvature between the ventricular electrodes and the atrial electrodes causing the latter to contact atrial tissue. One problem with this type of electrode system is that the electrical contact between the atrial electrodes and atrial tissue cannot be assured. It can, therefore, only be employed in VDD-systems and not in DDD-systems.

A similar electrode system is described in U.S. Pat. No. 4,154,247. The electrode lead in this electrode system is devised with more geometric variations at the atrial electrode. For example, the electrode lead in one embodiment is laid in a circle to enable the atrial electrode to establish continuous electrical contact with atrial tissue. In another embodiment, the electrode lead is S-shaped at the atrial electrode. Essentially the same problems occur with this electrode system. It cannot, therefore, be employed in a full range DDD-system.

SUMMARY OF THE INVENTION

An object of the present invention is to achieve an electrode system which can easily be implanted in a heart and which solves the above-described problems.

Another object of the invention is to achieve an electrode system which can easily be implanted in a heart and which simply and effectively ensures electrical contact between both atrial tissue and ventricular tissue.

A further object of the invention is to achieve an electrode system with a minimum number of electrode leads and which can be used in a range of different versions for both normal atrial pacing and defibrillation.

An electrode system in which electrical stimulation and/or sensing is assured in both the atrium and the ventricle is achieved in accordance with the invention wherein the atrial electrode is arranged at the distal end of the electrode lead and the ventricular electrode is arranged at a distance of 1 to 15 cm, preferably from 8 to 15 cm, from the distal end.

Placement of the atrial electrode at the distal end conveys the special advantage that the atrial electrode can be introduced into and affixed to tissue in the atrium before the ventricular electrode is advanced downwardly into the ventricle and affixed to the ventricular trabeculae. The portion of the electrode lead between the atrial electrode and the ventricular electrode is preferably made extremely flexible, so that it may be introduced into the ventricle to form a loop between the atrial electrode and the ventricular electrode. Thus implantation is simplified at the same time as good electrical contact with tissue in both the atrium and in the ventricle is assured.

The distance between the tip electrode (atrial electrode) and the ring electrode (ventricular electrode) is larger than in known electrode systems due to the extra curvature (and possible loop) of the electrode lead in the ventricle.

The orientation of the first contact and the second contact at the proximal end remains the same as in known electrode systems in order to permit the inventive electrode system to fit the lead connector of conventional stimulator apparatuses. This means that the connection between electrode and contact is only reversed at the end of the electrode lead, compared with known electrode systems.

Further, the area of the ring electrode surface in the inventive electrode system differs significantly from that in known electrode systems. For example, a ring electrode (atrial electrode) in a prior art electrode system may have an area of 20–35 mm$^2$ whereas the ring electrode (ventricular electrode) of the new inventive electrode system can have an area of 1–10 mm$^2$.

Since both the atrial electrode and the ventricular electrode are in secure electrical contact with tissue in both the atrium and the ventricle, the inventive electrode system can be used for all functions in a DDD-system with only one electrode lead. Moreover, this single electrode lead carries both the atrial and ventricular electrodes in-line, i.e., with no branching or other type of division of the single electrode lead.

A refinement of the electrode system is achieved in accordance with the invention in an embodiment wherein the electrode lead has an essentially semicircular curvature near the ventricular electrode, said curvature corresponding to the geometry of the heart in the implantation area.

The pre-shaped curved part of the electrode lead will be in the ventricle, where the electrode lead is laid in a loop. The curvature facilitates implantation of the electrode system and minimizes mechanical loads imposed on the heart by the electrode system after implantation.

Preferably the electrode lead is devised with a second curvature at the distal end. The second curvature preferably has an angle of curvature of 60° to 120° and curves in a direction opposite to the curvature near the ventricular electrode.

The atrial electrode is normally affixed to the upper part of the septum between the atria. At the distal end, a second pre-shaped curvature, which curves in the opposite direction to the curvature near the ventricular electrode, gives the electrode system a shape making it more suitable to its location in the heart. The second curvature also produces the advantage of making it easier for the physician implanting the electrode system to orient himself or herself with regard to the anatomy of the atrium, since the curved end of the distal part of the electrode lead makes it easier for the physician to find the coronary sinus, an orientation point during implantation. It may also be advantageous in some patients to place the atrial electrode in or near the coronary sinus.

The atrial electrode is appropriately devised with an active or passive first fixing device. To facilitate fixing of the ventricular electrode in the ventricle, it is an advantage to provide it with an active or a passive second fixing device. An active fixing device could consist of a screw or a hook, manipulated by a physician with a stylet and affixed to heart tissue during implantation of the electrode system. A passive fixing device could consist of fixed projection from the electrode lead at the electrodes, e.g., tines or fins. A passive fixation device ultimately becomes embedded in heart tissue. Such active or passive fixation devices have hitherto not been used for electrodes arranged at a distance from the end of the electrode lead. It should be noted that a ring electrode utilized as a ventricular electrode located in the ventricle will display other properties compared to a prior art ring electrode. Also, the conditions for tissue growth are somewhat different for ring electrodes located in the atrium and ring electrodes located in the ventricle, in particular when the ventricular ring electrode is located at the apex.

Another refinement of the electrode system is achieved in accordance with the invention in an embodiment wherein at least one additional atrial electrode is arranged on the electrode lead near the aforementioned atrial electrode and at least one additional first electrode conductor is arranged in the electrode lead in order to connect the additional atrial electrode to an additional first contact at the proximal end.

Alternatively, or as an additional complement, at least one additional ventricular electrode can be arranged on the electrode lead near the aforementioned ventricular electrode and at least one additional second electrode conductor is arranged in the electrode lead in order to connect the additional ventricular electrode to an additional second contact at the proximal end.

This yields a bipolar or multipolar system for both the atrium and the ventricle.

The range of uses for the electrode system is further extended in another embodiment of the electrode system according to the invention wherein at least one defibrillation electrode is arranged on the electrode lead between the atrial electrode and the ventricular electrode and/or between the ventricular electrode and the proximal end, and at least one defibrillation electrode conductor is arranged in the electrode lead in order to connect the defibrillation electrode to a defibrillation contact at the proximal end.

An electrode system for stimulating and sensing the heart, as well as defibrillating the heart, is hereby achieved on a single electrode lead, thereby greatly facilitating implantation and shortening implantation time. Furthermore, the electrode lead can be fixed within the heart in a manner previously not known, and the defibrillation electrodes will be held in a stable manner within the heart, thereby overcoming the problem described above.

Problems in the implantation of children are solved in accordance with the invention in that the electrode system, as described above, is devised so the electrode lead can be laid in a loop in a ventricle of the heart during implantation of the electrode system.

This thereby provides surplus electrode lead length inside the heart. As the child grows, a sufficient amount of lead is automatically withdrawn from the ventricle. No surgery is needed. For this purpose, preferably the electrode lead is devised with an essentially semicircular curvature at a distance of 1 to 15 cm, preferably 5 to 10 cm, from the distal end.

In conjunction with simultaneous measurement of a physiological variable and electrical stimulation/sensing in the atrium, a physiological sensor can be arranged on the electrode lead in order to sense the physiological parameter.

It is especially advantageous if the physiological sensor is arranged near the curvature in order to sense the physiological parameter in the ventricle.

A complete, multi-functional electrode system is achieved in accordance with the invention in an embodiment wherein the electrode system further includes at least one additional atrial electrode connected to at least one corresponding contact at the proximal end of the electrode lead and/or at least one ventricular electrode arranged near a curvature and connected to at least one corresponding contact at the proximal end of the electrode lead, and/or at least one defibrillation electrode arranged between the atrial electrode and the curvature and/or between the curvature and the proximal end and connected to at least one corresponding contact at the proximal end.

DESCRIPTION OF THE PREFERRED EMBODIMENTS

Figure 1:
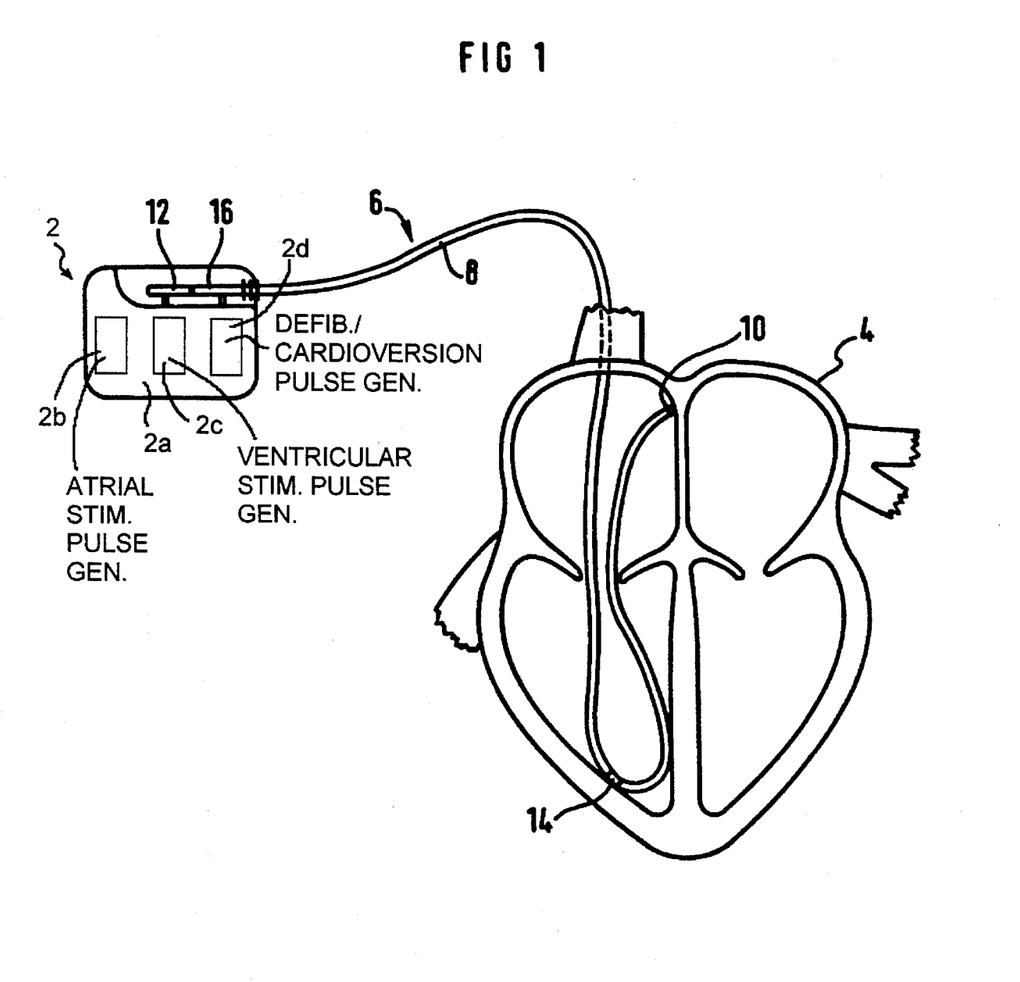
FIG. 1 shows a first embodiment of the inventive electrode system implanted in a heart.

FIG. 1 shows a medical electrical apparatus 2 which has been connected to a heart 4 with an electrode system 6. The medical electrical apparatus 2 may be a pacemaker such as a pacemaker operable in the DDD mode, a defibrillator, cardioverter, a combination pacemaker and defibrillator/cardioverter, or a diagnostic device. As is known, the medical apparatus 2 has a housing 2a of a size permitting implantation in a subject. The housing 2a contains an atrial stimulation pulse generator 2b, a ventricular stimulation pulse generator 2c and, if desired, a defibrillation/cardioversion pulse generator 2d. Known control circuitry (not shown) is employed to activate one or more of the generators 2b, 2c, and/or 2d as needed. The electrode system 6 includes an electrode lead 8 introduced into the heart 4 via the circulatory system. An atrial electrode 10 is connected to tissue in the atrium of the heart 4 and, via an electrode conductor (not shown), to a first contact 12 (leading to the atrial stimulation pulse generator 2b) at the proximal end of the electrode lead 8 for electrical connection to the medical electrical apparatus 2. A ventricular electrode 14 is connected to tissue in a ventricle of the heart 4 and, via an electrode conductor (not shown), to a second contact 16 (leading to the atrial stimulation pulse generator 2b) for electrical connection to the medical electrical apparatus 2. The distance between the atrial electrode 10 and the ventricular electrode 14 can be e.g., 12 cm. The portion of the electrode lead 8 between the atrial electrode 10 and the ventricular electrode 14 can also display a complete loop inside the ventricle. The special design of the electrode lead 8, with a reversed order of the atrial electrode 10 and the ventricular electrode 14, greatly facilitates implantation of the electrode system 6 and increases its functionality.

One or a plurality of stylet(s) can be used during the implantation. In principle, implantation is performed by advancing the electrode lead 8 into the heart 4 and affixing the atrial electrode 10 to tissue in the atrium, e.g., in the trabecular network. The part of the stylet between the atrial electrode 10 and the ventricular electrode 14 is then retracted into the electrode lead 8, and the electrode lead 8 is advanced into the heart 4 so the ventricular electrode 14 passes downwardly into the ventricle where it is subsequently affixed to ventricular tissue, preferably near the apex. During this operation, the electrode lead 8 can be allowed or forced to form a loop (not shown in this embodiment) within the ventricle.

The electrode lead 8 is specifically designed to be able to pass the tricuspid valve twice without causing any stress or irritation on heart tissue. Preferably, the end portion of the electrode lead 8, i.e., the portion between the ventricular electrode 14 and the atrial electrode 10 is made significantly thinner than the rest of the electrode lead 8. The thinner portion will cause only minor interference with the tricuspid valve leaflets. This can be made without any difficulty since there will be fewer conductors in the thinner portion (in the embodiment of FIG. 1, only one conductor).

The electrode system 6 can be used in a unipolar DDD-system, utilizing all DDD-functions in stimulating and sensing both the atrium and the ventricle in the heart 4. No reliable single lead DDD electrode system has hitherto been developed. The unipolar feature means that all pacing and sensing in the atrium and ventricle are made between the atrial electrode 10 and an indifferent electrode (not shown) on the pacemaker and between the ventricular electrode 14 and the indifferent electrode. Sensing can also be made atrioventricularly, however, between the atrial electrode 10 and the ventricular electrode 14. An electrode system utilizing bipolar possibilities is shown below. The electrode system 6 can, naturally, be utilized in other unipolar pacing systems as well, such as unipolar VDD-systems, etc.

Figure 2:
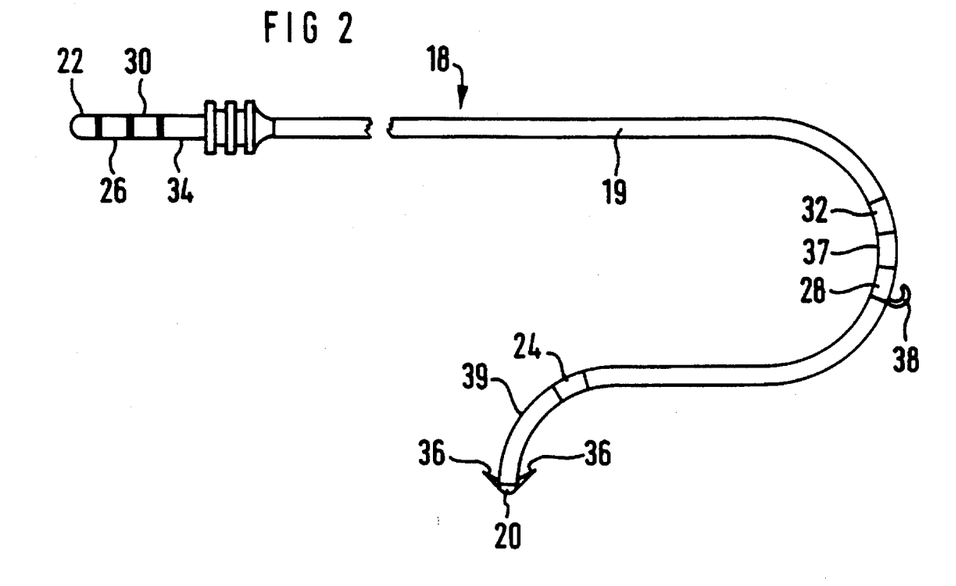
FIG. 2 shows a second embodiment of the inventive electrode system.

A second embodiment is shown in FIG. 2, in which the electrode system 18 has a first atrial electrode 20, electrically connected to a first contact 22, and a second atrial electrode 24, electrically connected to a second contact 26 at the proximal end of an electrode lead 19. The electrode system 18 further has a first ventricular electrode 28, electrically connected to a third contact 30, and a second ventricular electrode 32, electrically connected to a fourth contact 34. Near the atrial electrodes 20 and 24, the electrode system 18 has a passive fixation device 36 intended for attachment to the atrial trabecular network. Near the first ventricular electrode 28, the electrode system 18 has an active fixing device 38. The active fixing device 38 could, e.g., be an eccentric hook. One such active fixing device is described in European Application 0 570 712. Other known active fixing means can also be utilized with the electrode system 18.

The electrode system 18 has a first, semicircular curvature 37 near the ventricular electrodes 28 and 32 and a second curvature 39 near the atrial electrodes 20 and 24. The design with the curvatures 37 and 39 facilitates implantation of the electrode system 18 and reduces mechanical loads on the heart after implantation. Although the curvatures 37 and 39 are pre-shaped curves, the electrode lead 19 is itself very flexible and adapts smoothly to the shape of the interior of the heart.

The electrode system 18 can replace all bipolar electrode systems using two leads (one for the atrium and one for the ventricle). In particular, it can be utilized in bipolar DDD-systems, performing all DDD functions. If used with a pacemaker having an indifferent electrode on its housing, it can also utilize all unipolar functions described above in connection with FIG. 1.

Figure 3:
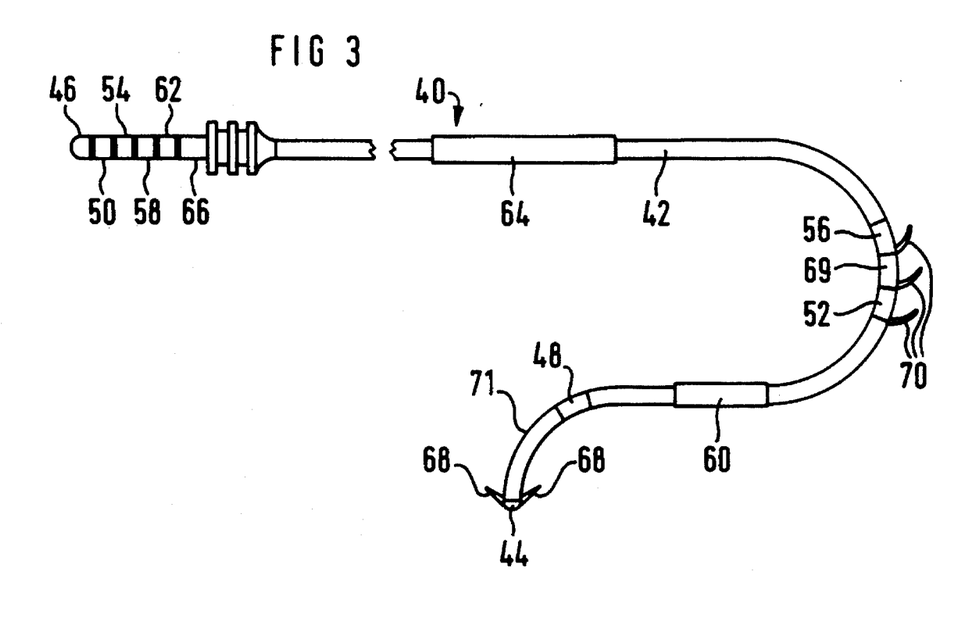
FIG. 3 shows a third embodiment of the inventive electrode system.

A third embodiment of the invention is shown in FIG. 3. The electrode system 40 shown therein has an electrode lead 42 with a distal end equipped with a first atrial electrode 44, electrically connected to a first contact 46, and a second atrial electrode 48, electrically connected to a second contact 50. Like the electrode system 18 in FIG. 2, the electrode system 40 has a first ventricular electrode 52, electrically connected to a third contact 54, and a second ventricular electrode 56, electrically connected to a fourth contact 58. A first passive fixing device 68 is arranged near the atrial electrodes 44 and 48, and a second passive fixing device 70 is arranged near the ventricular electrodes 52 and 56.

The electrode system 40 is intended for use with a defibrillator with pacing functions. For this purpose, the electrode system 40 also has a first defibrillation electrode 60, electrically connected to a fifth contact 62, and a second defibrillation electrode 64, electrically connected to a sixth contact 66. When inserted in the connection socket in the housing 2a (see FIG. 1), the contacts 62 and 66 will be in electrical contact with mating contacts in the housing 2a, leading to the defribillation/cardioversion pulse generator 2d, in a known manner. The first defibrillation electrode 60 has been placed at a distance from the distal end of the electrode lead 42, thereby positioning the first defibrillation electrode 60 in the ventricle after implantation, and the second defibrillation electrode 64 is arranged on the electrode lead 42 so it is positioned in the vena cava after implantation.

Regarding the pacing and sensing abilities, the electrode system can utilize all combinations described with the embodiments of FIGS. 1 and 2. The first defibrillation electrode 60 can replace the second ventricular electrode 56 for all its sensing and pacing functions and the second defibrillation electrode 64 can replace the second atrial electrode 48. The number of electrodes in the electrode system 40 can thus be reduced further, without losing any of its functional possibilities.

All known defibrillation activities for this kind of defibrillation system can be utilized. For example, atrial defibrillation can be effected between the first defibrillation electrode 60 and an indifferent electrode (not shown, but which can be any of the well known indifferent electrodes for defibrillation systems) and ventricular defibrillation can be effected between the second defibrillation electrode 64 and the indifferent electrode. Ventricular defibrillation can also be effected between the second defibrillation electrode 64 and the first defibrillation electrode 60, between the second defibrillation electrode 64 and the indifferent electrode interconnected with the first defibrillation electrode 60, and multi-potentially between the second defibrillation electrode 64 and both the indifferent electrode and the first defibrillation electrode 60 (whereby different voltages are utilized at the different points; the multi-potential defibrillation pulse can be biphasic, multi-phasic, sequential, etc.). It should be noted that for some of the defibrillation configurations, the indifferent electrode will act more as an active defibrillation electrode, in particular when multi-potential defibrillation pulses are used.

The first defibrillation electrode 60 and the second defibrillation electrode 64 can also be used for sensing functions. So called "vectorial sensing" can be made between each of the defibrillation electrodes 60 and 64 and the indifferent electrode. The sensing properties are enhanced due to the inventive arrangement of the electrode system. The first defibrillation electrode 60 will have a stable position since the portion of the electrode lead 42 carrying the first defibrillation electrode is anchored in both the atrium and the ventricle. (This also enhances the defibrillation function.) Not only sensing of the electrical activity, but also impedance measurements can be utilized in any combination of electrodes.

Thus, all pacing, sensing and defibrillation functions can be utilized with the electrode system 40, which has only one lead.

Figure 4:
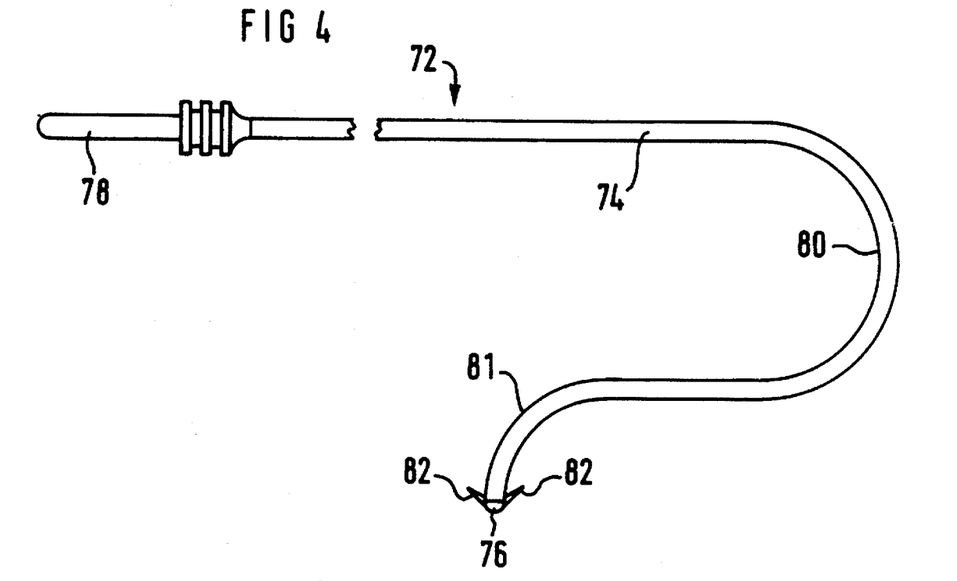
FIG. 4 shows a fourth embodiment of the inventive electrode system.

FIG. 4 shows a fourth embodiment of the invention. The electrode system 72 shown therein has an electrode lead 74, equipped at its distal end with an atrial electrode 76, electrically connected to a contact 78 at the proximal end of the electrode lead 74. The electrode lead 74 is devised so that part of the electrode lead 74 can be placed in a ventricle of the heart during implantation. In order to facilitate implantation, the electrode lead 74 has a first curvature 80 and a second curvature 82. The electrode system 72 is intended for implantation in a child. As the child grows the part of the electrode lead 74 in the ventricle is automatically drawn upwardly into the atrium. The number of operations needed during the child's growth can hereby be reduced to a minimum. In order to anchor the atrial electrode 76 in the atrium, the electrode system 72 has a passive fixing device 82.

Figure 5:
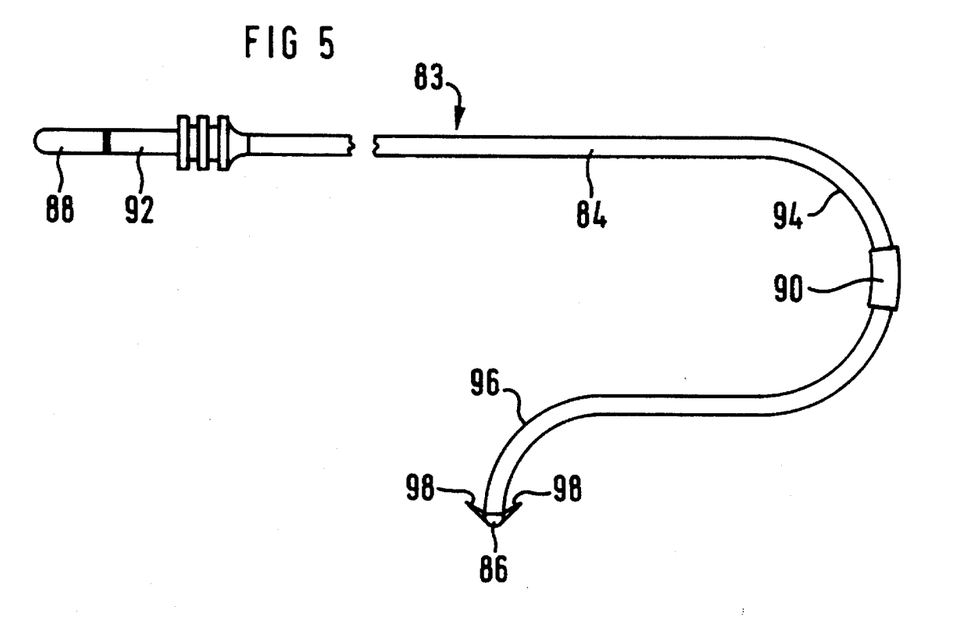
FIG. 5 shows a fifth embodiment of the inventive electrode system.

A fifth embodiment of the invention is shown in FIG. 5. The electrode system 83 shown therein has an electrode lead 84, which is equipped at its distal end with an atrial electrode 86, electrically connected to a first contact 88 at the proximal end of the electrode lead 84. In order to sense a physiological parameter, the electrode system 83 has a physiological sensor 90. The physiological sensor 90 could, e.g., sense blood pressure, blood temperature, blood flow, blood oxygen, blood pH or some other physiological parameter. The physiological sensor 90 is connected to a second contact 92 at the proximal end of the electrode lead 84. In this instance, the physiological sensor 90 has been placed on the electrode lead 84, so it comes to lie in a ventricle of the heart after the electrode system 83 is implanted.

As in previous embodiments, the electrode lead 84 has a first curvature 94 and a second curvature 96 to facilitate implantation of the electrode system 83 and to minimize mechanical loads on heart tissue after the implantation. In addition, the passive fixing device 98 is arranged at the distal end of the electrode lead 84 to affix the atrial electrode 86 to heart tissue in the atrium.

The electrode conductors (not shown) in the respective embodiments could be arranged in the electrode lead in some known manner, e.g., as parallel, helically coiled wires, electrically insulated from each other. Alternatively, the electrode conductors could run helically and concentricity (coaxially) in relation to one another in the electrode lead or as some combination thereof, i.e., both parallel and concentric, depending on the number of electrode conductors required.

The construction of electrode system is not limited to the above embodiments. The different features of the described embodiments can be combined in several ways, e.g., by having only a physiological sensor and defibrillation electrodes on the same electrode lead with fixing devices for attaching it in the atrium and ventricle, active and passive fixing devices can be combined in several different arrangements for fixing the different portions of the electrode lead to the heart tissue. The electrode system can also be equipped with more atrial and/or ventricular electrodes, thereby becoming multipolar in both the atrium and the ventricle. The number and location of defibrillation electrodes and the physiological sensor on the electrode lead can also be varied.

Although modifications and changes may be suggested by those skilled in the art, it is the intention of the inventors to embody within the patent warranted hereon all changes and modifications as reasonably and properly come within the scope of their contribution to the art.

I claim as my invention:

1. An electrode system implantable in a heart comprising:

an insulated electrode lead having a proximal end adapted for electrical and mechanical connection to a medical electrical apparatus, said proximal end having first and second electrical contacts, and said electrode lead having a distal end opposite said proximal end;

an atrial electrode carried on said electrode lead for electrical interaction with tissue in an atrium of a heart;

a first electrode conductor contained in said electrode lead and electrically connecting said atrial electrode and said first contact;

a ventricular electrode carried on said electrode lead for electrical interaction with tissue in a ventricle of said heart, said ventricular electrode having an exposed surface area in a range of 1–10 mm$^2$;

a second electrode conductor contained in said electrode lead and electrically connecting said ventricular electrode and said second contact; and said atrial electrode being disposed at said distal end of said electrode lead and said ventricular electrode being disposed in-line between said atrial electrode and said proximal end of said electrode lead at a distance in a range of 1 to 15 cm from said distal end of said electrode lead.

2. An electrode system as claimed in claim 1 wherein said ventricular electrode is disposed at a distance in a range from 8 to 15 cm from said distal end of said electrode lead.

3. An electrode system as claimed in claim 1 wherein said heart has an anatomical geometry, and wherein said electrode lead has a substantially semicircular pre-bent curvature at said ventricular electrode corresponding to said anatomical geometry of said heart.

4. An electrode system as claimed in claim 3 wherein said electrode lead has a further curvature at said distal end.

5. An electrode system as claimed in claim 4 wherein said further curvature has an angle of curvature in a range from 60° to 120° and is curved in a direction opposite to a direction of said curvature at said ventricular electrode.

6. An electrode system as claimed in claim 5 further comprising:

a defibrillation contact at said proximal end of said electrode lead;

a defibrillation electrode carried on said electrode lead in-line with said atrial electrode and said ventricular electrode; and a defibrillation conductor contained in said electrode lead and electrically connecting said defibrillation electrode and said defibrillation contact.

7. An electrode system as claimed in claim 1 further comprising means for actively fixing said atrial electrode to surrounding heart tissue.

8. An electrode system as claimed in claim 1 further comprising means for passively fixing said atrial electrode to surrounding heart tissue.

9. An electrode system as claimed in claim 1 further comprising means for actively fixing said ventricular electrode to surrounding heart tissue.

10. An electrode system as claimed in claim 1 further comprising means for passively fixing said ventricular electrode to surrounding heart tissue.

11. An electrode system as claimed in claim 1 further comprising:

a defibrillation contact at said proximal end of said electrode lead;

a defibrillation electrode carried on said electrode lead in-line with said atrial electrode and said ventricular electrode; and a defibrillation conductor contained in said electrode lead and electrically connecting said defibrillation electrode and said defibrillation contact.

12. An electrode system as claimed in claim 11 wherein said defibrillation electrode is disposed between said atrial electrode and said ventricular electrode on said electrode lead.

13. An electrode system as claimed in claim 11 wherein said defibrillation electrode is disposed between said ventricular electrode and said proximal end on said electrode lead.

14. An electrode system as claimed in claim 11 further comprising:

a further contact at said proximal end of said electrode lead;

a further atrial electrode carried on said electrode lead near said atrial electrode for electrical interaction with tissue in said atrium of said heart; and a further electrode conductor contained in said electrode lead and electrically connecting said further atrial electrode and said further contact.

15. An electrode system as claimed in claim 11 further comprising:

a further contact at said proximal end of said electrode lead;

a further ventricular electrode carried on said electrode lead near said ventricular electrode for electrical interaction with tissue in said ventricle of said heart; and a further electrode conductor contained in said electrode lead and electrically connecting said further ventricular electrode and said further contact.

16. An electrode system as claimed in claim 1 further comprising:

a further contact at said proximal end of said electrode lead;

a further atrial electrode carried on said electrode lead near said atrial electrode for electrical interaction with tissue in said atrium of said heart; and a further electrode conductor contained in said electrode lead and electrically connecting said further atrial electrode and said further contact.

17. An electrode system as claimed in claim 1 further comprising:

a further contact at said proximal end of said electrode lead;

a further ventricular electrode carried on said electrode lead near said ventricular electrode for electrical interaction with tissue in said atrium of said heart; and a further ventricular electrode conductor contained in said electrode lead and electrically connecting said further ventricular electrode and said further contact.

18. An electrode system implantable in a heart comprising:

an insulated electrode lead having a proximal end adapted for mechanical and electrical connection at an implantation site to a medical electrical apparatus, said proximal end having an electrical contact and said electrode lead having a distal end opposite said proximal end;

an atrial electrode carried on said electrode lead at said distal end for electrical interaction with tissue in an atrium of a heart;

an electrode conductor contained in said electrode lead and electrically connecting said atrial electrode and said electrical contact at said proximal end; and said electrode lead having a length for causing a portion of said electrode lead to form a loop in a ventricle of a heart when said atrial electrode is disposed in said atrium of said heart and said proximal end is disposed at said implantation site, said loop having a pre-bent semicircular curvature at a distance in a range of from 1 to 15 cm from said distal end of said electrode lead.

19. An electrode system as claimed in claim 18 wherein said pre-bent semicircular curvature is disposed in a range from 5 to 10 cm from said distal end.

20. An electrode system as claimed in claim 18 further comprising:
a physiological sensor carried on said electrode lead in line with said atrial electrode and disposed at said curvature for sensing a physiological parameter in said ventricle.

21. An electrode system as claimed in claim 20 wherein said electrical contact at said proximal end comprises a first electrical contact and wherein said electrode conductor comprises a first electrode conductor, said electrode system further comprising:
second and third electrical contacts at said proximal end of said electrode lead;
a further atrial electrode carried on said electrode lead in-line with said atrial electrode for electrical interaction with tissue in said atrium of said heart;
a second electrode conductor contained in said electrode lead and electrically connecting said further atrial electrode and said second electrical contact;
a ventricular electrode carried on said electrode lead in-line with said atrial electrode and said further atrial electrode and disposed within said loop for electrical interaction with tissue in said ventricle of said heart; and
a third electrode conductor contained in said electrode lead and electrically connecting said ventricular electrode and said third electrical contact.

22. An electrode system as claimed in claim 21 further comprising:
a defibrillation contact at said proximal end of said electrode lead;
a defibrillation electrode carried on said electrode lead in-line with said atrial electrode and said ventricular electrode; and
a defibrillation conductor contained in said electrode lead and electrically connecting said defibrillation electrode and said defibrillation contact.

23. An electrode system as claimed in claim 18 further comprising:
a defibrillation contact at said proximal end of said electrode lead;
a defibrillation electrode carried on said electrode lead in-line with said atrial electrode and said ventricular electrode; and
a defibrillation conductor contained in said electrode lead and electrically connecting said defibrillation electrode and said defibrillation contact.

24. An electrode system as claimed in claim 18 wherein said electrical contact at said proximal end comprises a first electrical contact and wherein said electrode conductor comprises a first electrode conductor, said electrode system further comprising:
second and third electrical contacts at said proximal end of said electrode lead;
a further atrial electrode carried on said electrode lead in-line with said atrial electrode for electrical interaction with tissue in said atrium of said heart;
a second electrode conductor contained in said electrode lead and electrically connecting said further atrial electrode and said second electrical contact;
a ventricular electrode carried on said electrode lead in-line with said atrial electrode and said further atrial electrode and disposed within said loop for electrical interaction with tissue in said ventricle of said heart; and
a third electrode conductor contained in said electrode lead and electrically connecting said ventricular electrode and said third electrical contact.

25. An electrode system as claimed in claim 24 further comprising:
a defibrillation contact at said proximal end of said electrode lead;
a defibrillation electrode carried on said electrode lead in-line with said atrial electrode and said ventricular electrode; and
a defibrillation conductor contained in said electrode lead and electrically connecting said defibrillation electrode and said defibrillation contact.

26. A system for pacing a heart comprising:
an implantable pacemaker operable in a DDD mode and having a connection location;
an electrode lead having a proximal end connected at said connection location to said pacemaker, and having a distal end opposite said proximal end;
an atrial electrode for electrical interaction with tissue in an atrium of a heart;
a ventricular electrode for electrical interaction with tissue in a ventricle of said heart;
said atrial electrode and said ventricular electrode being carried on said electrode lead in-line with each other with said ventricular electrode preceding said atrial electrode in a direction from said proximal end to said distal end; and
means for respectively electrically connecting said atrial electrode and said ventricular electrode to said pacemaker via said proximal end of said electrode lead.

27. A method for implanting a medical electrode lead in a heart comprising the steps of:
providing an electrode lead having a proximal end adapted for mechanical and electrical connection to a medical electrical apparatus and having a distal end opposite said proximal end;
disposing an atrial electrode, adapted for interaction with atrial tissue of a heart, at said distal end of said electrode lead;
inserting said electrode lead into said heart so that said atrial electrode is disposed in an atrium of said heart and inserting a length of said electrode lead through the tricuspid valve in said heart into a ventricle of said heart and forming a loop of said length of said electrode lead in said ventricle;
mechanically and electrically connecting said proximal end of said electrode lead to a medical electrical apparatus while leaving said loop in said ventricle; and
implanting said medical electrical apparatus.

28. A method as claimed in claim 27 comprising the additional step of passively fixing said atrial electrode in said atrium of said heart.

29. A method as claimed in claim 27 comprising the additional step of actively fixing said atrial electrode in said atrium of said heart.

30. A method as claimed in claim 27 comprising the additional step of passively fixing said loop in the ventricle of said heart.

31. A method as claimed in claim 27 comprising the additional step of actively fixing said loop in said ventricle of said heart.

32. A medical system implantable in a living subject comprising:

a housing adapted for a implantation in a living subject, said housing containing an atrial stimulation pulse generator for generating pulses for stimulating an atrium of a heart of said subject;

a ventricular stimulation pulse generator for generating pulses for stimulating an ventricle of said heart;

an insulated electrode lead having a proximal end adapted for electrical end mechanical connection to said housing, said proximal end having a first electrical contact electrically connected to said atrial stimulation pulse generator and a second electrical contact electrically connected to said ventricular stimulation pulse generator, and said electrode lead having a distal end opposite said proximal end;

an atrial electrode carried on said electrode lead for electrical interaction with tissue in the atrium of said heart;

a first electrode conductor contained in said electrode lead and electrically connecting said atrial electrode and said first electrical contact;

a ventricular electrode carried on said electrode lead for electrical interaction with tissue in the ventricle of said heart;

a second electrode conductor contained in said electrode lead and electrically connecting said ventricular electrode and said second electrical contact; and said atrial electrode being disposed at said distal end of said electrode lead and said ventricular electrode being disposed in-line between said atrial electrode and said proximal end of said electrode lead at a distance in a range of 1 to 15 cm from said distal end of said electrode lead.

33. A medical system as claimed in 32 further comprising:

a defribillation/cardioversion pulse generator contained in said housing for generating pulses for defribillating or cardioverting said heart;

a defribillation contact at said proximal end of said electrode lead electrically connected to said defribillation/cardioversion pulse generator;

a defribillation electrode carried on said electrode lead in-line with said atrial electrode and said ventricular electrode; and a defribillation conductor contained in said electrode lead and electrically connecting said defribillation electrode and said defribillation contact.

34. An electrode system implantable in a heart comprising:

an insulated electrode lead having a proximal end adapted for electrical and mechanical connection to a medical electrical apparatus, said proximal and having first, second and third electrical contacts, and said electrode lead a having distal end opposite said proximal end;

an atrial electrode carried on electrode lead for electrical interaction with tissue in an atrium of a heart;

a first electrode conductor contained in said electrode lead and electrically connecting said atrial electrode and said first contact;

a ventricular electrode carried on said electrode lead for electrical interaction with tissue in a ventricle of said heart;

a second electrode conductor contained in said electrode lead and electrically connecting said ventricular electrode and said second contact;

a defribillation electrode carried on said electrode lead;

a third electrode conductor contained in said electrode lead and electrically connecting said defribillation electrode and said third contact; and said atrial electrode being disposed at said distal end of said electrode lead and said ventricular electrode and said defribillation electrode being disposed in-line between said atrial electrode and said proximal end of said electrode lead, said ventricular electrode being disposed at a distance in a range of 1 to 15 cm from said distal end of said electrode lead.

* * * * *